United States Patent [19]

Sarazen

[11] 4,185,329
[45] Jan. 29, 1980

[54] WELDER'S SHIELD FOR ELECTRIC ARC WELDING

[76] Inventor: Philip R. Sarazen, 446 Lisgar St., Ottawa, Ontario, Canada

[21] Appl. No.: 838,919

[22] Filed: Oct. 3, 1977

[51] Int. Cl.² .......................... A61F 9/06; A61F 9/02
[52] U.S. Cl. ................................................. 2/8; 2/428
[58] Field of Search ...................... 2/8, 424, 427, 428; 128/142.7

[56] References Cited

U.S. PATENT DOCUMENTS

| | | | |
|---|---|---|---|
| 1,205,308 | 11/1916 | Work | 2/8 |
| 1,370,121 | 3/1921 | King | 2/8 X |
| 2,418,334 | 4/1947 | Coccellato | 2/8 |
| 3,232,290 | 2/1966 | Nicolai | 2/8 X |
| 3,430,262 | 3/1969 | Raschke | 2/8 |

FOREIGN PATENT DOCUMENTS 1190765  5/1970  United Kingdom ............................ 2/8

Primary Examiner—Peter P. Nerbun

[57] ABSTRACT

An improved welder's shield for electric arc welding comprising a flexible gasket secured to and protruding from the inside surface of the face mask. The gasket circumscribes the viewing window of the mask and flushly meets the face of the wearer about his eyes to provide a curtain thereabout and to prevent indirect radiation from being passed thereto by reflection or otherwise. The shield is preferably provided with a pivot point, when the face mask is secured to the head harness, located so that the mask, when being moved from or to face shielding position, is not obstructed in its movement by interference of the facial features of the wearer by the gasket.

11 Claims, 7 Drawing Figures

WELDER'S SHIELD FOR ELECTRIC ARC WELDING

BACKGROUND OF THE INVENTION

This invention relates generally to a welder's shield for electric arc welding, and more particularly concerns a welder's hood provided with means to reduce or prevent indirect radiation from being passed to the eyes of the wearer.

It is well known, even among welders, that the light from a welding arc is injurious to the eyes. Such a welding arc gives off ultra-violet and other harmful radiation which radiation may for example burn the retinas of the wearer's eyes. Consequently, the standard welding shield or helmet has a window of very dark glass to greatly reduce the radiation passing to the wearer's eyes from the arc. The welding shield may be of a type worn by the welder, e.g. being pivotally suspended from a headband, or may be of a type having a handle to be held with one hand of the welder in front of his face.

What is not so commonly known in the trade is the fact that indirect radiation from the arc may be passed to a welder's eyes, other than through the dark glass of the viewing means of the helmet, and that this indirect radiation may be very harmful to the welder's eyes. For instance, light from the arc may bounce off the welder's chest or a stainless steel tank or wall behind the welder, pass through the space between the welder's head and the inside surface of the face mask, and then be reflected off the inside surface of the mask or of the viewing window of the mask into the wearer's eyes; alternatively the arc from another welder may be reflected directly off of this window into the eyes of the first welder. After years of being subjected to such indirect radiation, the welder may not be able to weld for as long a period of time before he must stop to rest his eyes, and he may find the strength of his eyes has seriously deteriorated. Alternatively, often times this indirect radiation may have the same effect on the eyes of the welder as direct light from an arc, for example in conditions where this indirect light is of high intensity, e.g. welding in stainless steel tanks or with welders directly behind.

There are numerous helmets or shields described in the prior art, although few of these devices appear to provide a solution to the problem of this indirect radiation. For example, Canadian Pat. No. 392,792 of Schneider, issued Nov. 26, 1940 describes and illustrates a means associated with a welder's protective head mask for supplying fresh air to the wearer. The means comprises a cup, spring-mounted on the inside surface of the mask, urged towards the nose of the wearer and into flush engagement with the surface of the wearer's face about his nose. Fresh air is supplied to the wearer through hose means entering the cup.

Miscellaneous welders' shields, of general background interest, but which fail to provide a solution to the problem of harmful indirect radiation, include U.S. Pat. No. 2,578,171 of Bub, issued Dec. 11, 1951; U.S. Pat. No. 2,613,353 of Schnitzler, issued Oct. 14, 1952; Canadian Pat. No. 716,193 of Farr, issued Aug. 17, 1965; Canadian Pat. No. 911,652 of Raschke, issued Oct. 10, 1972; Canadian Pat. No. 938,001 of Finger, issued Dec. 4, 1973; and Canadian Pat. No. 989,216 of Feuk, et. al., issued May 18, 1976.

It is an object of the present invention to provide a welder's shield which will effectively protect the eyes of the wearer against indirect radiation which may be reflected to his eyes off the inside surface of the viewing window of the face mask or the inside surface of the mask. It is a further object of the present invention to provide such a helmet which will be both comfortable and operate effectively and conveniently if the wearer wishes to raise the mask to a position above the face or lower it into face shielding position.

SUMMARY OF THE INVENTION

In accordance with the invention, a welding shield is provided for use with an electric arc welding system comprising a flexible gasket secured to and protruding from the inside surface of the face mask. The gasket circumscribes the viewing window of the mask and flushly meets the face of the wearer and encircle his eyes to prevent indirect radiation from being passed thereto by reflection. The hood is preferably provided with a pivot point, if the face mask is of a type which is secured to a head harness, located so that the mask, when being swung from or to face shielding position, is not obstructed in its movement by interference of the facial features of the wearer with the gasket.

The gasket may be provided to surround merely the eyes of the wearer or alternatively the eyes and nose or eyes, noes and mouth of the wearer. In the latter instance, appropriate filter means, to remove hazardous particles or gases from the air inhaled by the wearer, may be provided in the sides of the gasket.

BRIEF DESCRIPTION OF THE DRAWINGS

Other objects and advantages of the invention will become apparent upon reading the following detailed description and upon referring to the drawings in which.

In the drawings, similar features have been given similar reference numerals.

While the invention will be described in connection with specific example embodiments thereof, it will be understood that it is not intended to limit the invention to that embodiment. On the contrary it is intended to cover all alternatives, modifications and equivalents as may be included within the spirit and scope of the invention as defined by the appended claims.

DETAILED DESCRIPTION OF THE INVENTION

Figure 1:
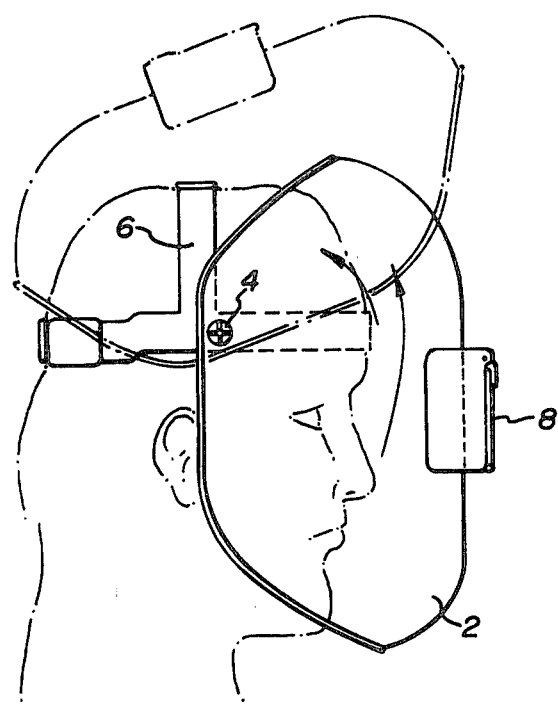
FIG. 1 is a side view of a standard known welder's shield shown in both face shielding position and a position raised above the face of the wearer.

Turning first to FIG. 1, there is shown a prior art helmet having face mask 2 pivotally secured at pivot 4 to head harness 6. Viewing means 8 consists of a window, preferably of a darkened or opaque glass, which permits the wearer to see the arc and the work area, but to shield his eyes, at the same time, from the ultra-violet radiation and other harmful radiation given off by the arc. This darkened glass may be hinged so that it may be swung out of position if the wearer wished to view his work, for example, without the darkened glass obstructing his view. The face mask shown in both face shielding position and position raised above the head of the welder includes frictional means for securing the helmet in either of these positions or positions intermediate thereto.

Figure 2:
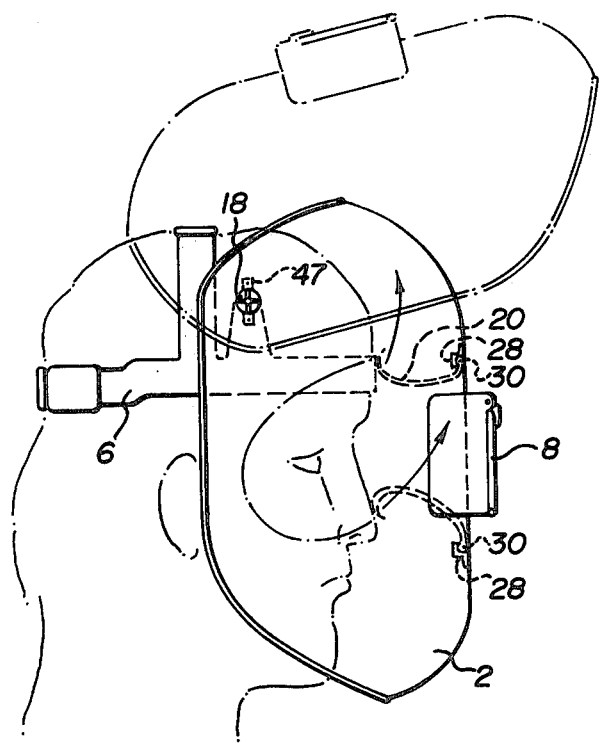
FIG. 2 is a side view of a welder's helmet according to the present invention, showing the face mask thereof in both face shielding position and positioned above the face of the wearer.

Turning to FIG. 2 there is shown a welder's shield according to the present invention having face mask 2 with front and side wall portions to extend in front of and to the sides of the face of the wearer. The face mask illustrated is pivotally secured to head band 6 at pivot means 18, for movement from a face shielding position to a position above the face of the wearer as shown in this FIG. (of course, this invention applies to other types of arc welding shields such as the hand-held type previously referred to). Pivot means 18 also permits adjustably securing the face mask in these positions or positions therebetween. Viewing means 8, consisting of a darkened or opaque glass window in the face mask, protects the eyes of the wearer against direct radiation from the welding arc, but permits him to see his work. Head band 6 is adjustable to fit the head of the wearer.

Figure 3:
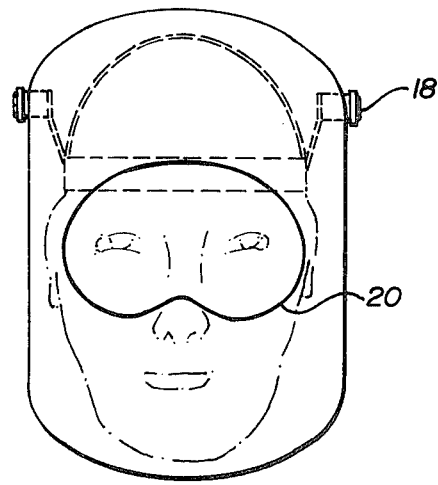
FIG. 3 is a front view of a welder's helmet of FIG. 2.

As shown in FIGS. 2 and 3, face mask 2 is provided with a tube-like flexible gasket 20 which is secured to and protrudes from the inside surface of face mask 2. This gasket encircles the eyes of the wearer so as to seal off completely all light passing to his eyes, except for that coming directly through the window. Gasket 20 may surround simply the wearer's eyes (FIGS. 2 and 3) or the wearer's eyes and nose (FIG. 4) or the wearer's eyes, nose and mouth (FIG. 5). Where the wearer's nose is surrounded by the gasket, appropriate one-way exhaust valves 22 and intake filter vents 24 may be provided in the wall of the gasket 20. The gasket 20 may be provided with appropriate means to permit replacement of the exhaust valves or filters with new ones.

Figure 6:
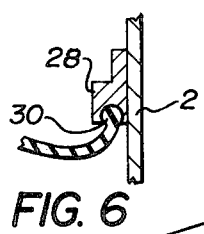
FIG. 6 is an enlarged fragmentary view of the connecting means for the gasket to the face mask.

The gasket is secured, by any appropriate means, to the inner face of the face mask 2. As seen in FIGS. 2 and 6, this means may be a Z-shaped bracket 28 provided to secure the perimeter of the face of the gasket 20 to the inner face of the face mask 2. This end of the gasket may be provided with a bead 30 which clips into bracket 28 to securely and, if desired, removably hold gasket 20 in place on the inner surface of face mask 2. Particularly where the gasket is intended to surround the wearer's eyes and nose as in FIGS. 4 and 5, the cooperation of gasket bead 30 with bracket 28 provides an air tight seal.

The opposite, free edge of gasket 20, as seen in FIG. 2, is tapered or feathered to make it pliable and permit it to form-fit around different facial features of the wearer.

It will be appreciated that by providing the inner surface of face mask 2 with appropriate brackets 28, for example a gasket 20 encircling only the wearer's eyes might be taken out and replaced by another gasket which encircled the wearer's eyes and nose or eyes, nose and mouth, so that a welder could select the desired gasket for a particular job, and clip it into place in appropriate brackets 28.

Figure 4:
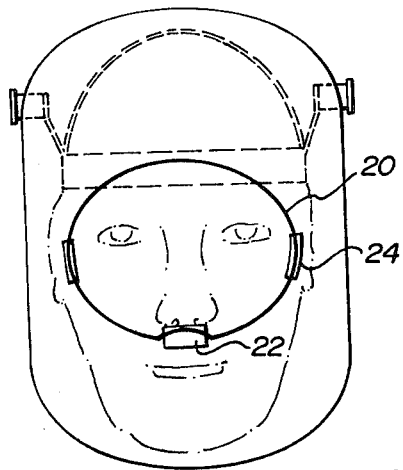
FIGS. 4 and 5 are schematic, front views of alternative embodiments of a welder's helmet according to the present invention.
Figure 5:
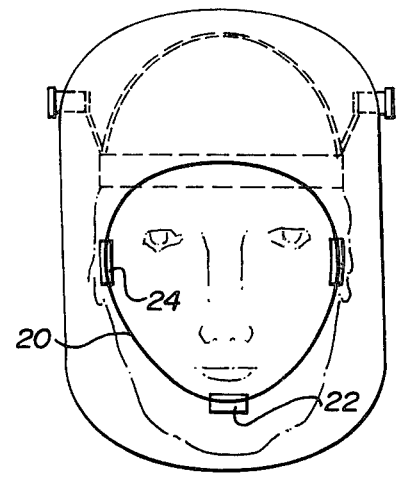

The welder's shields of FIGS. 4 and 5 are intended for application for example where noxious gases are produced as in welding galvanized metal or oily materials or in welding the inside of tanks or inside of ships.

The embodiment of FIG. 4, where just the wearer's eyes and nose are encircled by gasket 20, permits the welder to talk while he works. Although not illustrated, such nose-encircling gasketed shields may additionally be provided with means for delivering fresh air to the gasket and thence to the wearer.

If the standard welding helmet of FIG. 1 were fitted with such gaskets as shown in FIGS. 2 to 5, the welder would not be able to swing the mask over his head without scraping his face; swinging the mask downwards would present a similar problem (see arrows). As shown in FIG. 2, the welding shield of the present invention provides a pivot 18 which is raised and somewhat forward in respect of the location of the pivot of the standard helmet. It is not neccessary that pivot 18 be located in this forward position. The positioning of pivot 18 is such as to permit the mask to be raised from or lowered to the face shielding position in such a way that the gasket does not scrape the wearer's facial features and is not obstructed thereby (see arrows) as would be the case if the pivot were located as in FIG. 1. This location of pivot 18 ensures that the inner edges of gasket 20, adjacent the wearer's face, are swung outward, beyond the wearer's facial features, in the initial stages as the face mask is swung upright out of face shielding position. This requires, in addition, that the sides of face mask 2 be constructed to enable pivot point 18 to operate with a horizontal axis.

Figure 7:
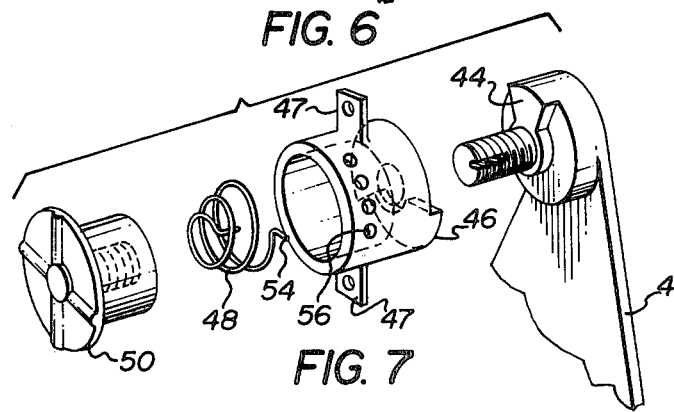
FIG. 7 is an enlarged exploded view of a pivot means used to connect a face mask to a head band in a welder's helmet according to the present invention.

In order to keep the gasket close to the face, pivot 18 is provided with means complementing a standard brake mechanism of the type associated with the pivot 4 of a standard helmet (FIG. 1) to urge the inner edge of the gasket gently towards the wearer's face as the face mask reaches face shielding position. Such a device is shown in FIG. 7, where pivot 18 is made up of head band extension 42 with appropriate raised frictional surface 44, cooperating frictional surface 46 (secured to face mask 2 by tabs 47), spring 48 and adjusting knob 50. As long as frictional surfaces 44 and 46 bear against each other, under adjustable, lateral urging from spring 48, the face mask may be secured in any desired position merely by turning adjustment knob 50 to increase or decrease the frictional engagement of surfaces 44 and 46. As the face mask 2 approaches face shielding position however, frictional surface 44 passes off of cooperating surface 46 and is positioned opposite lowered surface 54 (when these parts are in the orientation shown in FIG. 6) so that rotational bias of spring 48 overcomes any remaining frictional forces in pivot 18 and gently urges mask 2 towards the wearer's face. By positioning the base 54 of spring 48 in one of adjustment holes 56 the amount of bias urging the face mask and gasket 20 towards the wearer's face may be adjusted.

Thus it is apparent that there has been provided, in accordance with the invention, a welder's hood for electric arc welding that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

I claim as my invention:

1. A welder's shield for use with an electric arc welding system, the shield comprising a face mask having front and side wall portions for extending in front and to the sides of the face of a wearer, and viewing means in the mask to protect the eyes of the wearer against direct radiation from the arc but to permit him to see his work, the improvement comprising a flexible gasket protruding from the inside surface of the face mask, the base of which gasket includes separable fastening means cooperating with mating fastening means on the inside surface wherein said gasket is removably secured to that inside surface, the gasket circumscribing the viewing means, to flushly meet the face of the wearer and encircle his eyes to prevent indirect radiation from being reflected thereto, the shield further comprising a head harness and the mask being directly secured to the head harness by a pivot located on a vertical extension that projects above the head encircling portion of the harness for unobstructed movement of the shield from a position above the face of the wearer to a face shielding position or vice versa, manually operable means for adjustably securing the face mask in these positions or positions therebetween.

2. A welding shield according to claim 1, wherein the pivot point for the face mask is located so that the mask, when being moved from or to face shielding position, lifts away from the face of the wearer so that his normal facial features do not obstruct movement of the gasket and mask.

3. A welder's shield according to claim 1, wherein means are provided for urging the face mask gently towards the face of the wearer when the face mask is at and near face shielding position for flush engagement of the gasket with the face of the wearer.

4. A welder's shield according to claim 3, wherein a spring means cooperates with the adjustable securing means of the face mask to urge the face mask towards the face of the wearer as the face mask approaches face shielding position.

5. A welding shield according to claim 1, wherein the side of the gasket which contacts the wearer's face is tapered to increase its flexibility and provide improved contact with the face of the wearer.

6. A welder's shield according to claim 1, wherein the gasket is to circumscribe only the eyes of the wearer.

7. A welder's shield according to claim 1, wherein the gasket is to circumscribe only the eyes and nose of the wearer.

8. A welder's shield according to claim 1, wherein the gasket is to circumscribe only the eyes, nose and mouth of the wearer.

9. A welder's shield according to claim 8, wherein the gasket is further provided with filter means to remove impurities from the air breathed by the wearer.

10. A welder's shield according to claim 9, wherein the filter means is replaceable.

11. A welder's shield according to claim 1, wherein a bracket means removably secures the gasket to the inner surface of the face mask.

* * * * *